United States Patent
Jin et al.

(10) Patent No.: US 11,486,871 B2
(45) Date of Patent: Nov. 1, 2022

(54) METHOD FOR SPECIFYING WATER BLOCK REMOVAL AGENTS FOR HYDROCARBON RESERVOIRS

(71) Applicant: Alchemy Sciences, Inc., Houston, TX (US)

(72) Inventors: Luchao Jin, Houston, TX (US); Shashidhar Rajagopalan, Fulshear, TX (US); James Russum, Sugar Land, TX (US)

(73) Assignee: ALCHEMY SCIENCES, INC., Houston, TX (US)

( * ) Notice: Subject to any disclaimer, the term of this patent is extended or adjusted under 35 U.S.C. 154(b) by 240 days.

(21) Appl. No.: 17/021,058

(22) Filed: Sep. 15, 2020

(65) Prior Publication Data
US 2021/0080442 A1 Mar. 18, 2021

Related U.S. Application Data

(60) Provisional application No. 62/900,788, filed on Sep. 16, 2019.

(51) Int. Cl.
*G01N 33/24* (2006.01)
*E21B 49/08* (2006.01)

(52) U.S. Cl.
CPC ......... *G01N 33/246* (2013.01); *E21B 49/088* (2013.01)

(58) Field of Classification Search
CPC .................... G01N 33/246; E21B 49/088
See application file for complete search history.

(56) References Cited

U.S. PATENT DOCUMENTS

| | | | |
|---|---|---|---|
| 7,220,709 B1* | 5/2007 | Qu ........................... | C09K 8/74 166/305.1 |
| 7,549,472 B2* | 6/2009 | Morrow .................... | C09K 8/82 166/305.1 |
| 8,739,877 B2* | 6/2014 | Robb ....................... | C09K 8/602 166/305.1 |
| 9,624,422 B2* | 4/2017 | Dams .................... | C09K 8/5751 |
| 10,197,489 B2* | 2/2019 | McCarty ................. | C09K 8/66 |
| 2011/0174485 A1* | 7/2011 | Robb ..................... | C09K 8/685 166/270.1 |
| 2017/0030879 A1* | 2/2017 | Yu ........................... | G01N 1/28 |
| 2019/0309216 A1* | 10/2019 | Jin .......................... | E21B 43/16 |
| 2021/0032987 A1* | 2/2021 | Seltzer ................... | G01R 33/12 |

OTHER PUBLICATIONS

Penny et al. "Nanofluid System Improves Post Frac Oil and Gas Recovery in Hydrocarbon Rich Gas Reservoirs," SPE-154308 (Year: 2012).*

(Continued)

*Primary Examiner* — John Fitzgerald
(74) *Attorney, Agent, or Firm* — Ewing & Jones, PLLC

(57) ABSTRACT

A method includes determining reservoir rock and fluid characteristics of a reservoir rock and, based on the reservoir rock and fluid characteristics of the reservoir rock, selecting a core. The method also includes selecting a first surfactant and selecting a second surfactant. In addition, the method includes performing a water block mitigation test using the selected core, the first surfactant and the second surfactant and performing a proppant phase trapping mitigation test using the selected core, the first surfactant and the second surfactant.

17 Claims, 4 Drawing Sheets

(56) References Cited

OTHER PUBLICATIONS

Abrams et al. "From the Laboratory to the Field: Successful Multistage Horizaontal Fracturing Design and Implementation in Tight Sandstones in the Anadarko Basin," SPE-173379-MS (Year: 2015).*

Liang et al. "The Applicability of Surfactants on Enhanding the Productivity in Tight Formations," SPE-178584-MS (Year: 2015).*

Longoria, R. A. et al., "Water Blocks in Tight Formations: The Role of Matrix/Fracture Interaction in Hydrocarbon-Permeability Reduction and Its Implications in the Use of Enhanced Oil Recovery Techniques"; SPE Journal 2017, 22(05), pp. 1393-1401.

* cited by examiner

METHOD FOR SPECIFYING WATER BLOCK REMOVAL AGENTS FOR HYDROCARBON RESERVOIRS

This application is a non-provisional application which claims priority from U.S. provisional application No. 62/900,788, filed Sep. 16, 2019, which is incorporated by reference herein in its entirety.

FIELD

This disclosure relates generally to the field of treatment fluids used in hydraulic fracturing subterranean formations during hydrocarbon recovery. More specifically the disclosure relates to methods for selecting chemicals used in treatment fluids.

BACKGROUND

Certain traditional hydrocarbon production operations use water-based treatment fluids in the wellbore. These traditional hydrocarbon production operations include, but are not limited to, drilling, completions, stimulation, and hydraulic fracturing. The water-based treatment fluids may enter the surrounding near-wellbore areas of the formation, damage the formation, and detrimentally affect production via water blocking, i.e., trapping of aqueous and hydrocarbon phases in the invaded zone of the formation around the wellbore and within the proppant pack. Water blockages may form in both the matrix adjacent to the fracture and in the fracture itself. These water blockages have a negative impact on relative permeability and effective fracture lengths, reducing well productivity. The water blockages may occur in oil or gas production wells, in the proppant pack, in the induced and natural fracture, or in the pore matrix. The specific manifestation of the water blockages and the impact of those water blockages on the traditional hydrocarbon production operations vary according to such factors as connate (or residual or irreducible) water saturation, the phase behavior of the combination of the aqueous phase and non-aqueous phase fluids, operating parameters, rock characteristics, and matrix-fracture interactions.

Without being bound by theory, it is conventionally believed that water block results from an interaction of capillary forces and drawdown pressure. In unconventional reservoirs, for example, when the drawdown pressure does not sufficiently exceed the capillary pressure, water blockage may occur.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily reduced for clarity of discussion.

SUMMARY

Figure 1:
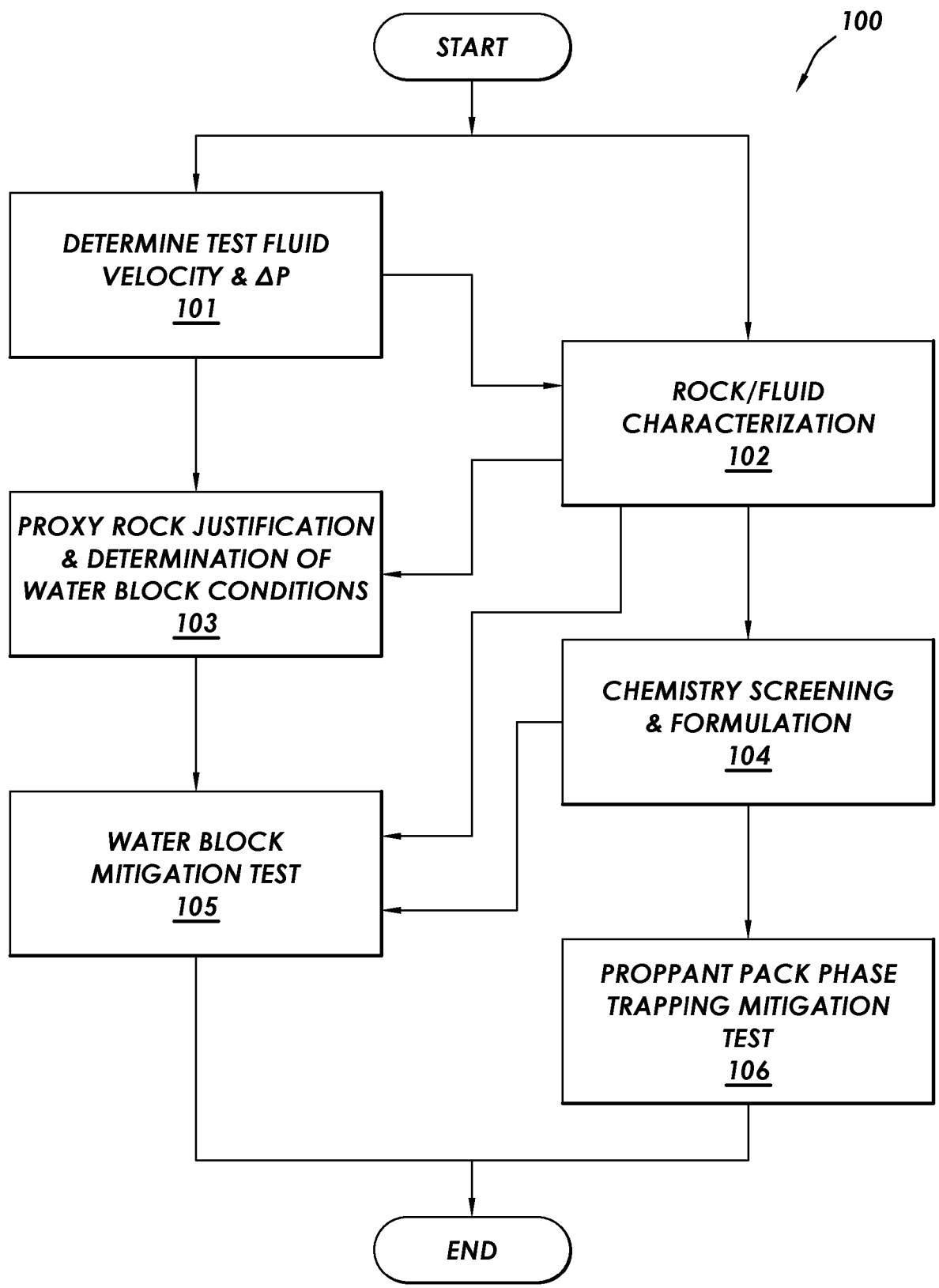
FIG. 1 is a flow diagram of a screening method for specifying a chemical treatment for the remediation of water block in hydrocarbon bearing reservoirs in accordance with at least one embodiment of the present disclosure.
Figure 2:
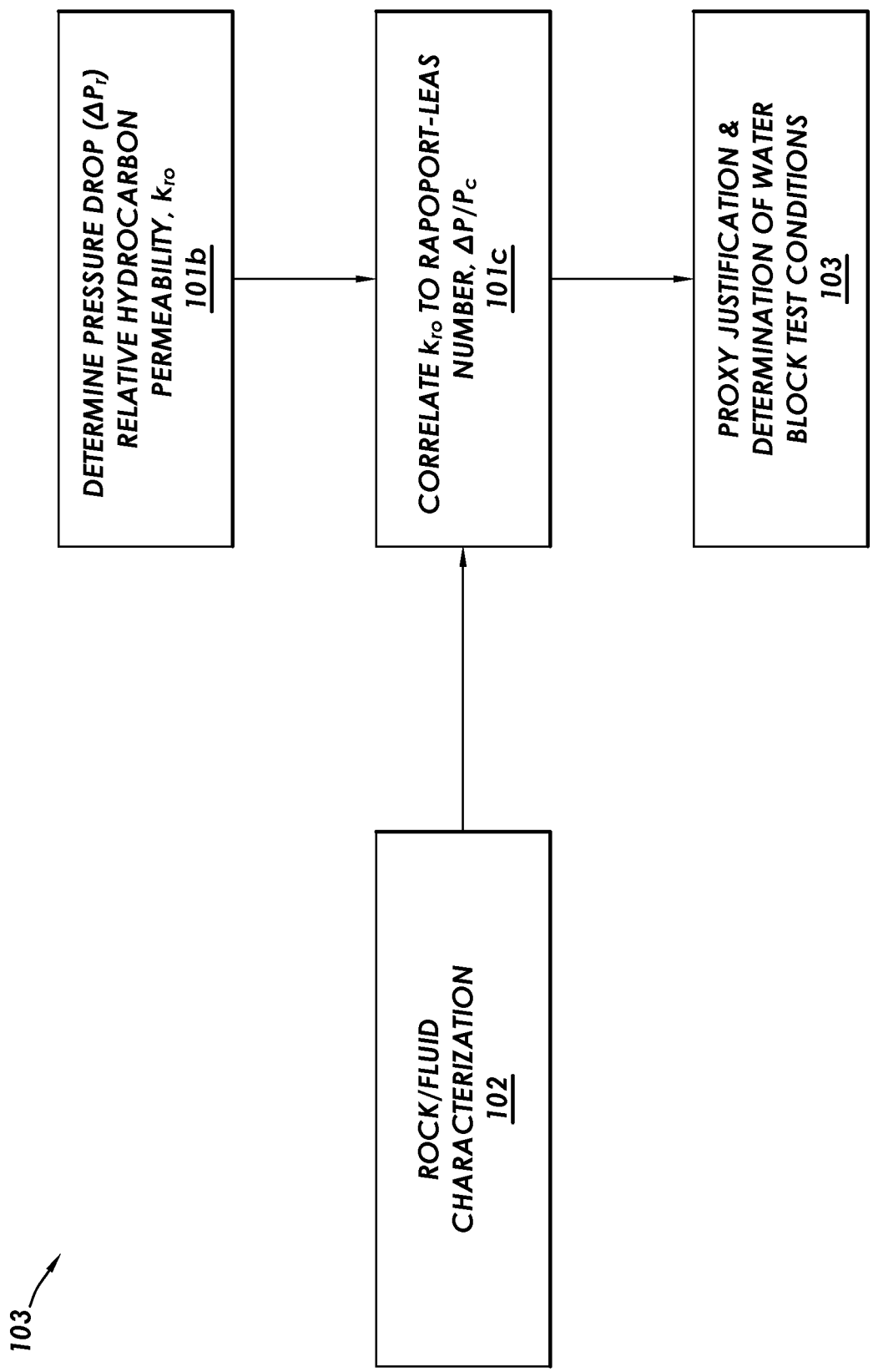
FIG. 2 is a flow diagram of a process to determine the flow velocity and pressure drop along the fracture half-length and fracture-matrix interface in accordance with at least one embodiment of the present disclosure.

A method is disclosed. The method includes determining reservoir rock and fluid characteristics of a reservoir rock and, based on the reservoir rock and fluid characteristics of the reservoir rock, selecting a core. The method also includes selecting a first surfactant and selecting a second surfactant. In addition, the method includes performing a water block mitigation test using the selected core, the first surfactant and the second surfactant and performing a proppant phase trapping mitigation test using the selected core, the first surfactant and the second surfactant.

DETAILED DESCRIPTION

The following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

This disclosure is not limited to the embodiments, versions, or examples described, which are included to enable a person having ordinary skill in the art to make and use the disclosed subject matter when the information contained herein is combined with existing information and technology.

Further, various ranges and/or numerical limitations may be expressly stated below. It should be recognized that unless stated otherwise, it is intended that endpoints are to be interchangeable. Further, any ranges include iterative ranges of like magnitude falling within the expressly stated ranges or limitations. For example, if the detailed description recites a range of from 1 to 5, that range includes all iterative ranges within that range including, for instance, 1.3-2.7 or 4.9-4.95.

FIG. 1 depicts specification method 100, which includes a method for the characterization, analysis, screening and performance testing of chemical treatments for water block remediation in hydrocarbon bearing reservoirs. As used herein, "reservoir rock" refers to, without limitation, both the medium or high porosity and permeability rock associated with conventional reservoirs and source rock or unconventional reservoirs integrated with the source rock with low porosity and low permeability rock associated with unconventional reservoirs.

Figure 3:
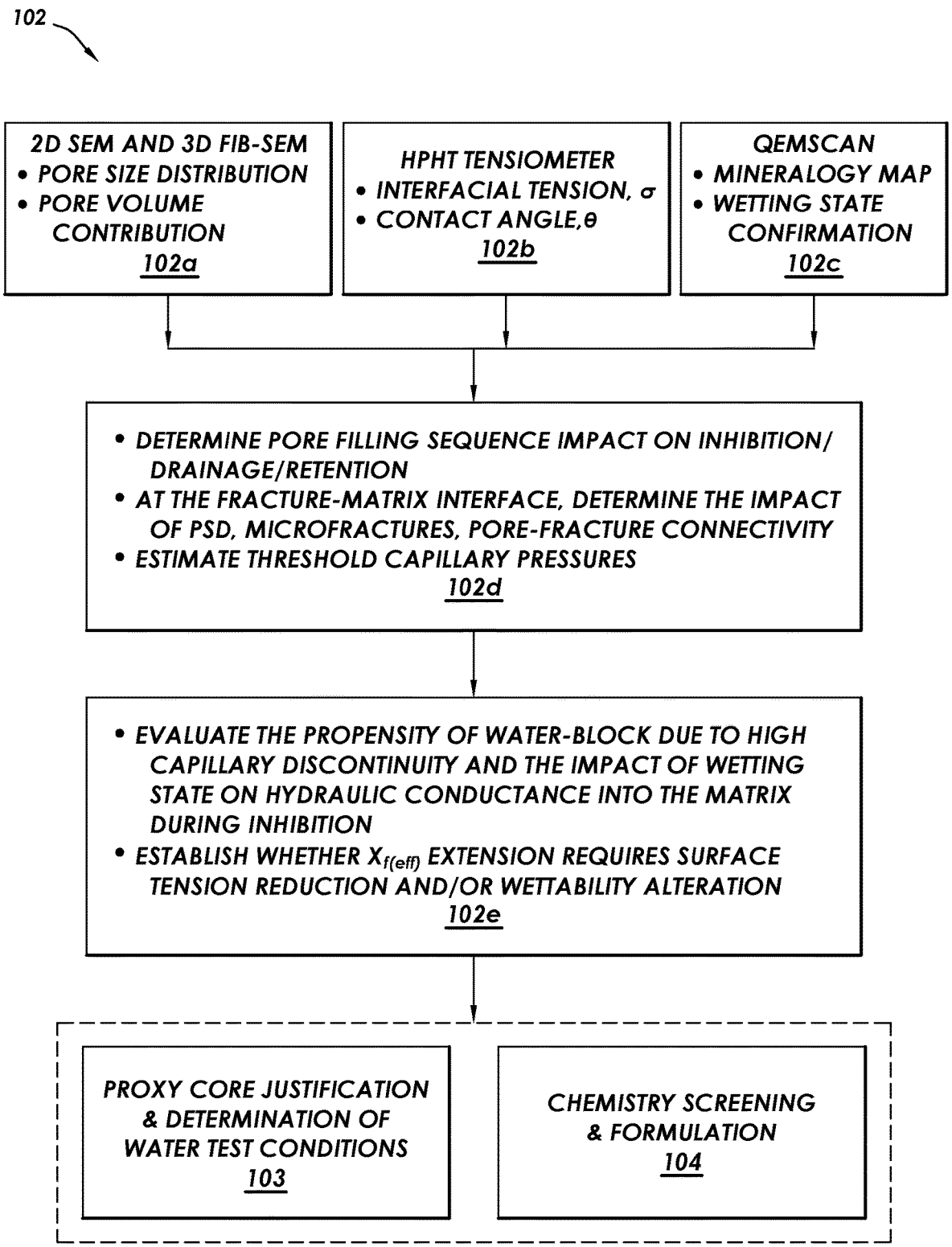
FIG. 3 is a flow diagram of a process for characterizing reservoir properties from a reservoir rock sample consistent with at least one embodiment of the present disclosure.

Specification method 100 includes determination of fluid velocity and pressure drop $\Delta P$ step 101. In determination of fluid velocity and $\Delta P$ step 101, fluid velocity through the fracture to the wellbore and $\Delta P$ between reservoir rock matrix and hydraulic fracture are determined following the steps depicted in FIG. 3. As shown in FIG. 3, in determine pressure drop between reservoir matrix and hydraulic fracture step 101b, the pressure drop between reservoir matrix and fracture, ($\Delta P_r$) is calculated, for instance using reservoir simulation software. The capillary pressure $P_c$ of the reservoir rock sample is determined in rock/fluid characterization step 102. Using the method described in Longoria, R. A.; Liang, T.; Huynh, U. T.; Nguyen, Q. P.; DiCarlo, D. A., Water Blocks in Tight Formations: The Role of Matrix/ Fracture Interaction in Hydrocarbon-Permeability Reduction and Its Implications in the Use of Enhanced Oil Recovery Techniques. SPE Journal 2017, 22 (05), 1393-1401, the dimensionless Rapoport-Leas number ($\Delta P/P_c$) of a reservoir formation from its matrix to hydraulic fracture is calculated and used to determine the water block onset hydrocarbon relative permeability $k_{ro}$ in step 101c. With further attention to FIG. 1, the water block onset conditions are then used to select the pressure drop using a proxy rock that acts as an analog for the reservoir rock if the reservoir rock does not have adequate porosity and permeability according to:

$$\frac{\Delta P_R}{P_{cR}} = \frac{\Delta P_P}{P_{cP}}$$

where $\Delta P_R$ is the reservoir pressure drop (from the simulation), $P_{cR}$ is the capillary pressure in the reservoir, $P_{cP}$ is the calculated capillary in the test using a proxy rock in proxy rock justification step 103. With these three values, the pressure drop in the proxy rock test, $\Delta P_P$, can then be set. In another embodiment, the reservoir rock can be used directly if the porosity and permeability of the reservoir rock are appropriate. In such an embodiment the step 103 may be omitted.

Figure 4:
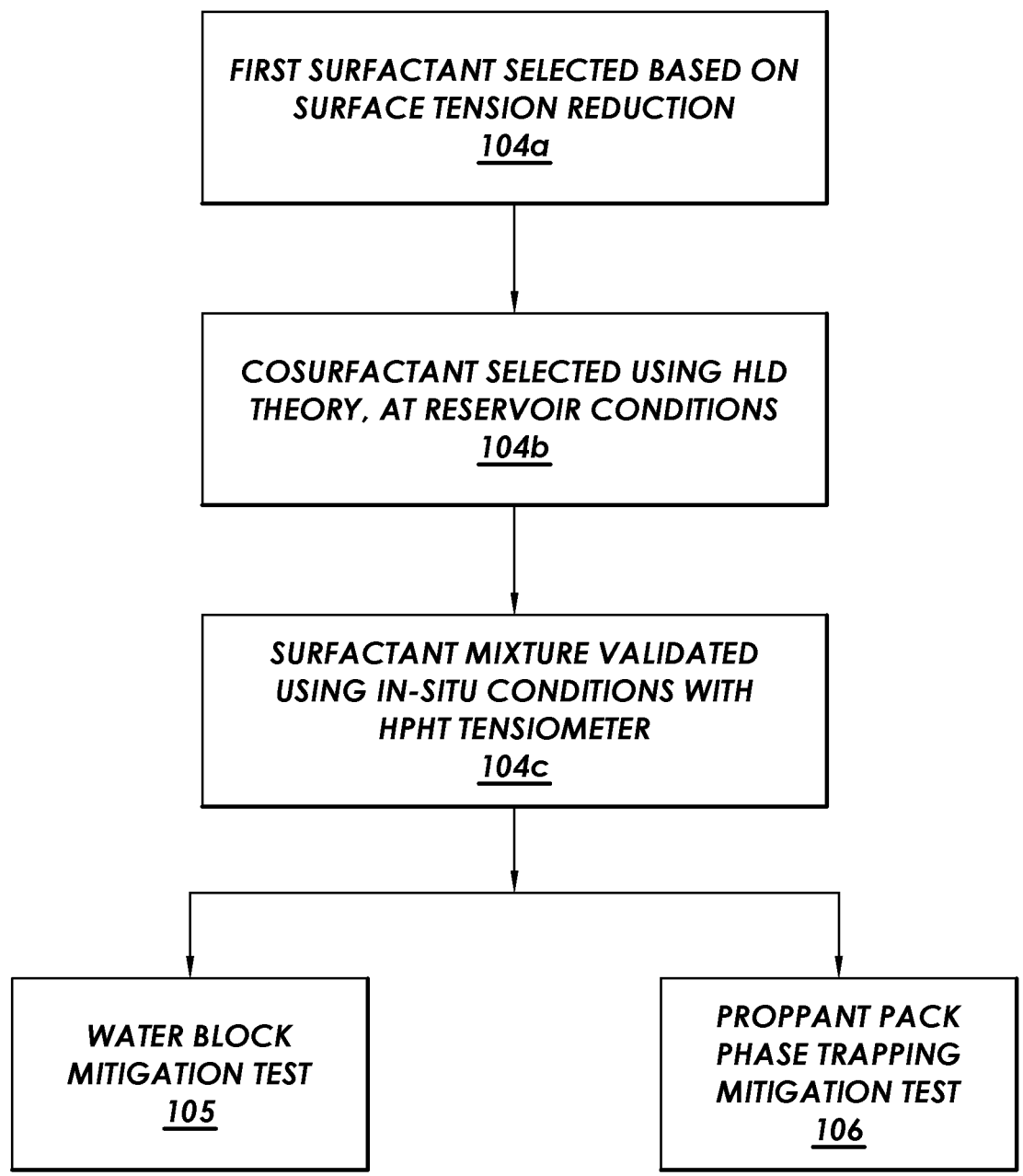
FIG. 4 is a flow diagram of a process for screening surfactant blends for water block mitigation consistent with at least one embodiment of the present disclosure.

In rock/fluid characterization step 102, shown in FIGS. 1 and 4, the rock and fluid characteristics of a reservoir rock are determined. Two- and three-dimensional characterization of reservoir rock samples using Scanning Electron Microscopy (2D SEM) and Focused Ion Beam Scanning Electron Microscopy (3D FIB-SEM) is conducted in 2D SEM and 3D FIB-SEM step 102a to determine the pore size distribution (PSD), the pore volume contribution, and the pore/microfracture connectivity of the reservoir rock sample. X-Ray Diffraction (XRD) and Quantitative Evaluation of Materials by Scanning Electron Microscopy (QEMSCAN) are performed to qualitatively and quantitatively characterize the mineralogy of the reservoir rock sample in QEMSCAN step 102c. In HPHT Tensiometer step 102b, in-situ wettability is characterized utilizing contact angle measurement at reservoir conditions with reservoir rock samples, and in-situ interfacial tension between aqueous and hydrocarbon phases is measured at reservoir condition with reservoir fluid samples. Using the information derived from 3D FIB-SEM step 102a and HPHT Tensiometer step 102b, in pore characterization step 102d, the effect of pore filling sequence on imbibition, draining, and retention is determined. Further, in pore characterization step 102d, the impact of PSD, microfractures, and pore-fracture connectivity is determined for the fracture-matrix interface. Further, the threshold capillary pressures are calculated. Using the information from step 102d, in water block evaluation step 102e, the propensity of water block due to high capillary pressure, capillary discontinuity, and the impact of wetting state on hydraulic conductance into the matrix during imbibition is calculated, as well as establishing whether $X_{f(eff)}$ extension requires interfacial tension reduction and/or wettability alteration. Brine imbibition in step 102e is performed with an Amott cell test to evaluate the wettability of reservoir rock sample. Gas and fluid compositions are collected before step 102. With the rock and fluid characterization of steps 102d and 102e, the propensity for water block can be evaluated. The rock and fluid characterization of steps 102d and 102e are issued as guidance for proxy rock justification and determination of water block test conditions step 103, and chemical treatment raw material screening step 104.

After steps 101 and step 102 are completed, a proxy rock sample for laboratory testing can be selected using step 103 based on the PSD, pore volume distribution, porosity, permeability and mineralogy. The pressure drop determined in step 101 is used in the water block mitigation test step 105.

In step 104, a mixture of surfactants are selected using surface tension reduction (gas/liquid at ambient) and interfacial tension (IFT) at reservoir temperature and salinity. A first surfactant is selected by analyzing the reduction in surface tension using a representative brine at ambient conditions in first surfactant selection step 104a. HLD (Hydrophilic-Lipophilic Difference) theory is utilized to select a second surfactant in step 104b—selection of cosurfactant and determine the ratio of the two surfactants that will result in the lowest IFT at reservoir temperature and salinity using in-situ conditions in validate surfactant mixture step 104c.

In water block mitigation test 105, a high pressure, high temperature two-phase core flooding apparatus is used. Based on the selected rock, a core is selected. For example, if a proxy rock is used, the core may be obtained from the proxy rock. If the reservoir rock is used, a core may be obtained from the reservoir rock. The high temperature two-phase core flooding apparatus may use a micro-CT scanner capable of 700 nm resolution, enabling imaging of in-situ flow and fluid occupancy within the core. The pressure drop used in the core flood test is the pressure drop determined in step 101. Initially, the core may be completely saturated with brine, e.g. water saturation $S_w=1$, at reservoir temperature and pressure. Then primary drainage may be conducted using methane to establish the initial brine saturation, $S_{wi-1}$. In the first flood cycle, brine may be injected, mimicking treatment fluid injection, to establish the residual gas saturation, $S_{gr-1}$, or residual oil saturation, $S_{or-1}$. The first flood cycle is followed by hydrocarbon injection to mimic hydrocarbon production and measure the residual water saturation, $S_{wi-2}$. The second flood cycle uses brine dosed with a blend of the two surfactants, followed by another hydrocarbon injection where residual gas saturation, $S_{gr-2}$, or residual oil saturation, $S_{or-2}$ is measured. The residual water saturation after the second cycle, $S_{wi-3}$, is compared to $S_{wi-2}$ to evaluate the efficacy of the blend of the two surfactants. Finally, the proxy rock core is scanned to determine if the water block mitigation test negatively impacted the integrity of the core.

In proppant pack phase trapping mitigation test step 106, a high pressure, high temperature three-phase miniature core-flooding apparatus integrated with a high-resolution (from 64 µm to 700 nm) X-ray micro-CT scanner may be used. A core may be cut and packed with proppant to replicate a hydraulic fracture. Two miniature core samples are cut from reservoir rock plugs using a saw, creating a simulated fracture along the length of each miniature core sample. As used herein, "miniature core samples" means core samples that are smaller than for traditional core-flood tests. Each miniature sample is then packed with 2 to 3 layers of proppant that have representative mesh size and sphericity to form a propped sample. The propped samples may be then wrapped with Teflon tape and heat shrink tube to hold the assembly together. Two 200 mesh (70 µm) screens may be placed at the inlet and outlet faces of the miniature core samples. The proppant-packed fractured core sample is sonicated and cleaned with an appropriate solvent mixture. The proppant pack porosity and fracture average area and aperture are obtained through high-resolution micro-CT images. Steady-state absolute permeability of the proppant pack to brine is measured using a flow through technique. First cycle of the experiments is performed by conducting a base waterflood followed by hydrocarbon injection. Pressure drops during these processes are recorded and in-situ saturation and pore-fluid occupancy maps are obtained. Second cycle of the experiments is performed by conducting a surfactant flood followed by hydrocarbon injection. Pressure drops during these processes are recorded and in-situ saturation and pore-fluid occupancy maps are obtained.

During the first cycle of step 106, the proppant pack is first flooded with an aqueous phase of brine to establish 100% water saturation. This step represents the hydraulic fracturing stage before depletion takes place. The pressure drop values recorded at this stage are used to calculate the absolute permeability of the proppant pack to brine. Depletion is commenced by injecting hydrocarbon (unsteady-state drainage) at the flow rate established in step 101. The initial water saturation ($S_{wi}$) and the effective hydrocarbon permeability ($k_{rg}/k_{ro}$ at $S_{wi}$) are measured at the end of the primary drainage. Three-dimensional maps of fluid occupancy at the end of the steps in the cycle are obtained.

The second cycle of step 106 is conducted by following the same procedure as the first cycle, with the exception of an aqueous phase consisting of a mixture of brine and the water block chemical formulation from 104. After fully saturating the proppant pack with the chemical/brine solution, the system is subjected to an unsteady-state hydrocarbon injection process with the same flow rate as the previous cycle. Again, the initial water saturation ($S_{wi}$) and the effective hydrocarbon permeability ($k_{rg}/k_{ro}$ at $S_{wi}$) are measured at the end of the primary drainage. Three-dimensional maps of fluid occupancy are again obtained at the end of the steps in the second cycle.

The hydrocarbon permeabilities of the two cycles are compared, along with the three-dimensional occupancy maps, to determine the efficacy of the surfactant blend.

EXAMPLES

Example 1

Rock/Fluid Characterization

Pore size distribution and Pore volume contribution: A sample of rock sample A was obtained. 2-D and 3-D SEM images of the reservoir rock sample A were obtained at nanometer resolutions, i.e., 5-20 nm. A dual-beam Helios 650 Nanolab FIB-SEM instrument was used to image rock sample A with electron beams at 2 KV and 100 PA energy levels using a TLD detector at Back Scatter Electron (BSE) mode. The surface of the sample was milled and smoothened using ion beams prior to imaging. The 2-D and 3-D SEM images had fields of view (FOV) of 50×50 and 20×20×7.5 µm, respectively.

The SEM images were imported to Avizo 9.4 software for processing and further analysis. A Non-local Means filter was applied on the images to remove the salt and pepper noises and generate smoother data sets. An Interactive Thresholding method was used to segment the images to i) pore space, ii) organic matter (OM), and iii) clay & OM cement. Based on these images, the vast majority of the pores were found to be formed between calcite grains and were determined to be inorganic pores. Therefore, these pores were likely to be water-wet.

The pore size distribution (PSD) of the reservoir rock was obtained through quantitative analysis of 3-D SEM images. Pores with a diameter ranging from 10 to 40 nm (average: 25 nm) were found to be the most frequent pores. Based graphing, the PSD peak was found and it was determined that nano-fractures with apertures in the range of 200-600 nm had the highest volume contribution to the pore space.

Interfacial tension and contact angle: Interfacial tension (IFT) and contact angle (CA) values of brine/methane/rock system were measured by rising/captive bubble tensiometry enhanced by video-image digitization technique. The test apparatus included a Hastelloy high pressure and temperature measurement visual cell, a high-resolution camera, a Yamato oven, a dual-cylinder 5000-series Hastelloy Quizix pump to supply stable flow rates and pressures during the measurements, and a dual cylinder Isco pump (500 D-series) to increase the pressure of methane to the experimental conditions. The measurement cell was placed on an anti-vibration table. To establish the experimental conditions, the cell was wrapped with heating jacket, which was connected to the temperature control unit. A bubble of methane was created inside the measurement cell (Gas-in-Brine method) through a needle (e.g., 0.56 mm outside diameter). Images of gas bubbles were captured with time at a constant interval (e.g., 30 seconds) to measure the interfacial tension. The captured images were analyzed to obtain IFT values using the Axisymetric Drop Shape Analysis (ADSA) software by fitting the drop profile to the Young-Laplace equation For CA measurements, the rock substrate was mounted on the rock sample holder inside the measurement cell and the cell was subsequently filled with the brine solution. Methane was then injected into the measurement cell though a needle (1.26 mm outside diameter) approaching the surface from below (captive bubble method). Images of the gas bubbles were captured at 30 seconds intervals when the bubbles were placed beneath the rock surface using a Quizix pump. The captured images of bubbles were analyzed by ImageJ software and the CA was determined by measuring the angles made by the tangent line on the bubbles toward the aqueous phase. Contact angles were measured for several droplets and the average value at 5000 psi and 250° F. was 34.56±6.93. The contact angle values indicated a water-wet condition for the rock sample.

Mineralogy: The mineralogy of the reservoir rock was obtained using X-Ray powder Diffraction (XRD) and Quantitative Evaluation of Minerals by SCANning electron microscopy (QEMSCAN) techniques. In the XRD method, the analyzed material was finely ground, homogenized, and average bulk composition was determined. According to the peaks of the relative intensity, the reservoir rock sample A appeared to be a sandy carbonate mainly composed of calcite. The peak of quartz indicated that the sample consisted of some quartz as well.

To evaluate the mineralogy of the reservoir rock quantitatively, the 2-D mineralogy maps of the rock were obtained using a QEMSCAN 650F from FEI. These analyses generated 3.0 mm by 3.0 mm maps of the mineralogy of the sample with an optical resolution of 2 µm per pixel. In the course of sample preparation, two rock substrates (1 cm×1 cm) were cut from the reservoir rock samples. The substrates were then mechanically polished using a polishing apparatus at 50 rpm. Silicon carbide powder and diamond suspension were used during the polishing process to generate a smooth rock surface and to remove irregular and uneven areas created during the cutting process. The rock substrates were mounted on Aluminum flats stubs using a conductive, double-side carbon tape and silver paint. The samples were coated with carbon to prevent any electron charging during imaging. Calcite was the dominant mineral by areal percentages higher than 82%. The results of mineralogy analysis were later used to select an appropriate proxy for use in the water blockage experiments.

Example 2

Determine Test Fluid Velocity & ΔP

A reservoir simulation model was set up to calculate the pressure drop from matrix to fracture. The pressure drop from matrix to fracture ($\Delta P_R$) at $x_f$ of 10 ft was found to be 2500 psi. The capillary pressure at reservoir condition ($P_{cR}$) was obtained by converting mercury injection capillary pressure (MICP), following the equation below:

$$P_{cR} = \frac{(\sigma \cos\theta)_R}{(\sigma \cos\theta)_{MICP}} P_{c_{MICP}}$$

Interfacial tension σ and contact angle θ of MICP were obtained from literature and that of gas-brine-reservoir for the gas formation were obtained in Example 1. The data are listed in the Table 1.

TABLE 1

| Condition | Interfacial tension σ, mN/m | Contact Angle, θ |
|---|---|---|
| MICP | 480 | 130 |
| Gas-Brine-Reservoir | 28 | 35 |

Example 3

Proxy Rock Justification & Determination of Water Block Test Conditions

Tope Ledfe Cottonwood was selected as proxy to replace the reservoir rock for use in the water blockage experiments. The proxy rock was mainly composed of calcite which is similar to the reservoir rock, and the reservoir rock was initially water-wet. The proxy rock was imaged at high-resolution using a micro-CT scanner to obtain the pore size distribution of the proxy rock. Pores with a diameter of 5 μm were found to be the most frequent pores. Pores with diameters ranging from 5-20 μm had the highest contribution to the pore space volume.

The dimensionless Rapoport-Leas number ($\Delta P/P_c$) of a reservoir formation from its matrix to hydraulic fracture was calculated and used to determine the water block onset conditions, following the equation below:

$$\frac{\Delta P_R}{P_{cR}} = \frac{\Delta P_P}{P_{cP}}$$

In this case, $$\Delta P_P = \Delta P_R \frac{P_{cP}}{P_{cR}}$$

Capillary pressure is a function of pore size distribution (r), according to Young-Laplace equation as below:

$$P_c = \frac{2\sigma\cos\theta}{r}$$

Because the proxy core has similar wettability and interfacial condition are the same as reservoir rock condition, $$\Delta P_P = \Delta P_R \frac{r_R}{r_P}$$

where $r_R$ is the pore size of reservoir rock and $r_p$ is the pore size of the proxy rock.

The pore size distributions of proxy rock and reservoir rock were synchronized by factoring and lining up the highest frequency peaks. A synchronization factor of 25 was obtained, so that the capillary pressure of proxy rock was estimated to be 1/25 of the reservoir rock. The pressure drop at the water bock test was determined to be 100 psi.

Example 4

Chemistry Screening & Formulation

Surfactant candidates were screened by surface tension measurement. 250 ppm surfactant solutions were prepared with formation brine. Surfactant A with lowest surface tension was selected for further formulation.

Surfactant A was mixed with different co-surfactants and formulated to four formulations. Equal volumes of 0.5 wt % formulations and oil were combined in quartz tubes at various salinity. The tubes were put to a water bath and heated. The tubes were hand shaken to mix the aqueous solutions and oil and left in the water bath to equilibrate for 2 weeks. The phase volumes were determined by measuring the levels of each phase in the tubes. The optimum salinity of each formulation was found to vary with temperature.

Example 5

Water Block Mitigation Test

A high-pressure, high-temperature two-phase core-flooding apparatus was used to perform the experiments. Prior to initiating the flooding, the core plug was dried and weighed. The core sample was then placed in the core holder and an initial confining stress of 1,000 psi was applied. The porosity of the sample was measured under 1,000 psi net confining stress using an in-line helium porosimeter and was found to be 14.67%. Afterwards, the net confining stress was reduced to 500 psi and CO2 was injected into the core to remove air from the pore space and the connected lines. The core and connected tubing were then vacuumed for 24 hours to remove CO2 from the system. Subsequently, the core was fully (100%) saturated with blank brine by injecting several pore volumes of the fluid and increasing the pore pressure (to 1,000 psig) to dissolve any trapped CO2. The temperature, pore pressure, and overburden pressure were increased to 250° F., 5,000 psig, and 6,000 psig, respectively. The experimental conditions were maintained for the rest of the experiments, unless the core was removed to be weighed. When the experimental conditions were established, the absolute brine permeability of the porous medium was measured by recording pressure drop responses at various brine flow rates.

Primary drainage was performed by injecting gas into the system. This step was carried out to establish and represent reservoir initial conditions prior to hydraulic fracturing. The primary drainage started with a low flow rate of gas, e.g., 0.02 cc/min, and increased by steps to a final value of 1.15 cc/min. The water saturation ($S_{wi-1}$) was measured and the pressure drop was also recorded.

Two main groups of experiments were targeted in this test. Under the first group (Cycle 1), an imbibition process was conducted by injecting the blank brine (WF1) to establish residual gas saturation ($S_{gr-1}$). Afterward, a primary drainage (PD1) process was commenced by injecting gas while the brine injection was halted (unsteady-state flow regime). The gas injection process was started with a low flow rate and when the differential pressure reached to almost 300 psi, the injection mode was changed to constant pressure delivery and the gas flow rate was monitored. When the flow rate was near 0.5 cc/min, the injection mode was changed to constant flow rate and the gas flow rate was maintained at 0.5 cc/min until the pressure drop across the core became stable. At this stage, the gas flow rate was increased to 1.15 cc/min to establish the initial water saturation ($S_{wi-2}$). The pressure drops were recorded and the gas relative permeability ($k_{rg-1}$) at $S_{wi-2}$ was measured. The core was then removed from the core holder and weighed to obtain water saturation ($S_{wi-2}$).

The core was loaded back into the core holder and the temperature and pressure of the setup were again raised to pre-specified values. At this point, the second group of the experiments were initiated. The surfactant solution was injected into the core and to establish the residual gas saturation (Sgr-2). Afterward, secondary drainage (SD) process was carried out by injecting gas under a procedure similar to the one used in the first group of experiments to obtain the Swi-3 and the $k_{rg-2}$ at $S_{wi-3}$. At this stage, the experiment was considered complete, the pressures and temperature were dropped to ambient conditions and the core was taken out and weighed to determine $S_{wi-3}$. The core sample was scanned to check its integrity at the end of the experiments. The residual gas saturations ($S_{gr-1}$ and $S_{gr-2}$) were determined by measuring the amount of water recovered from the core and collected in the cell during the corresponding flow processes.

The results are summarized in Table 2, showing the relative permeability of gas was increased from 0.683 to 0.814, because of the addition of designed surfactant formulation into the fracturing fluid.

TABLE 2

| Step No. | Process | Description | $S_w$ | $S_g$ | $k_w$ | $k_g$ |
|---|---|---|---|---|---|---|
| 1 | Brine injection | Inject brine to establish $S_w$ = 1 | 1 | 0 | 1 | — |
| 2 | Primary drainage | Inject gas to establish $S_{wi}$ | 0.294 | 0.706 | — | 0.694 |
| 3 | Imbibition | Inject 0.37 PV of brine to mimic fracturing fluid injection | 0.653 | 0.347 | — | — |
| 4 | Drainage | Inject gas to mimic gas production | 0.300 | 0.700 | — | 0.683 |
| 5 | Imbibition | Inject 0.37 PV of surfactant solution to mimic fracturing fluid injection | 0.616 | 0.384 | — | — |
| 6 | Drainage | Inject gas to mimic gas production | 0.256 | 0.744 | — | 0.814 |

Example 6

Proppant Pack Phase Trapping Mitigation Test

Two miniature core samples were cut from 38-mm-diameter reservoir core plugs. Afterwards, a precision saw was utilized to create a fracture along the length of each sample. Each sample was then packed with 2 to 3 layers of 40/70-mesh sand proppants. The propped samples were wrapped with Teflon tape and heat shrink tube to hold the assembly firmly. Two 200 mesh (70 µm) screens were placed at the inlet and outlet faces of the sample to suppress migration of any proppant and/or shale fragments toward the core holder fittings and production lines.

After placing the sample in the core holder, an initial confining stress of 5,000 psi was applied. The entire core was scanned at 10 µm resolution at this stage of the experiments and the acquired images were further used to select one location of interest to be scanned repeatedly during the flow experiments. The region of interest (ROI) was then imaged at 7.5 µm resolution. This image set was used as reference to analyze the images obtained during the two-phase flow experiments. The core was then fully (100%) saturated with the blank brine by injecting several pore volumes of the fluid and subsequently increasing the pore pressure (to 1,000 psi). The temperature of the core holder was increased to 140° F. at this stage and maintained for the rest of the experiments. Absolute brine permeability of the medium was measured by recording pressure drop responses at various brine flow rates under experimental conditions (1,000 psi and 140° F.). Afterward, primary drainage was performed by injecting gas into the system. Under the second cycle, the same procedure was followed while using 0.5 gpt surfactant solution instead of blank brine. During each step, after the system reached steady state conditions, the medium was scanned, and the initial water saturation was calculated directly from the micro-CT images. The pressure drop data was also recorded during these steps to obtain effective permeability to gas. The residual water saturation was to 43% from 74% with the introduction of surfactant solution. Effective permeability for gas to flow increases from 464 mD to 606 mD.

The foregoing outlines features of several embodiments so that a person of ordinary skill in the art may better understand the aspects of the present disclosure. Such features may be replaced by any one of numerous equivalent alternatives, only some of which are disclosed herein. One of ordinary skill in the art should appreciate that they may readily use the present disclosure as a basis for designing or modifying other processes and structures for carrying out the same purposes and/or achieving the same advantages of the embodiments introduced herein. One of ordinary skill in the art should also realize that such equivalent constructions do not depart from the spirit and scope of the present disclosure and that they may make various changes, substitutions, and alterations herein without departing from the spirit and scope of the present disclosure.

The invention claimed is:

1. A method comprising:
   determining reservoir rock and fluid characteristics of a reservoir rock;
   based on the reservoir rock and fluid characteristics of the reservoir rock, selecting a rock;
   selecting a first surfactant;
   selecting a second surfactant;
   selecting a core from the rock;
   performing a water block mitigation test using the selected core, the first surfactant and the second surfactant; and
   performing a proppant phase trapping mitigation test using the selected core, the first surfactant and the second surfactant.

2. The method of claim 1, further comprising the step of determining pressure drop between a reservoir matrix and a hydraulic fracture, the step comprising:
   calculating a pressure drop of a reservoir matrix, ($\Delta P_r$) of the reservoir rock;
   calculating the dimensionless Rapoport-Leas number ($\Delta P/P_c$) of a reservoir formation of the reservoir rock from matrix to hydraulic fracture; and
   correlating $k_{ro}$ using water block onset conditions, wherein $k_{ro}$ is the water block onset hydrocarbon relative permeability.

3. The method of claim 1, wherein the step of performing a proppant phase trapping mitigation test comprises using a three-phase core-flooding apparatus integrated with an X-ray micro-CT scanner.

4. The method of claim 1, wherein the step of determining reservoir rock and fluid characteristic comprises:
   characterizing in-situ interfacial tension/surface tension measurement at reservoir conditions with a sample of the reservoir rock.

5. The method of claim 1, wherein selecting a rock is performed by using the reservoir rock or preparing a proxy rock.

6. The method of claim 5, wherein preparing a proxy rock is performed by setting a pressure drop in the proxy rock according to the equation:

$$\frac{\Delta P_R}{P_{cR}} = \frac{\Delta P_P}{P_{cP}}$$

where $\Delta P_R$ is the reservoir pressure drop (from the simulation), $P_{cR}$ is the capillary pressure in the reservoir, $P_{cP}$ is the calculated capillary in a test using a proxy rock in proxy rock justification, and $\Delta P_P$ is a pressure drop in the proxy core.

7. The method of claim 1, wherein the step of selecting the first surfactant comprises:
   choosing the first surfactant; and
   analyzing the reduction in surface tension of the selected rock using a representative brine and the first surfactant.

8. The method of claim 7, wherein the step of selecting the second surfactant comprises:
   choosing a second surfactant; and
   determining a ratio of the first surfactant and second surfactant that results in the lowest IFT at reservoir temperature and salinity.

9. The method of claim 1, wherein the step of performing a water block mitigation test comprises using a two-phase core flooding apparatus.

10. The method of claim 9 further comprising imaging in-situ flow and fluid occupancy of the selected core.

11. The method of claim 1, wherein the step of determining reservoir rock and fluid characteristics comprises:
    using three dimensional Focused Ion Beam Scanning Electron Microscopy (3D FIB-SEM) to determine the pore size distribution (PSD), pore volume contribution, and pore/microfracture connectivity of a reservoir rock sample of the reservoir rock.

12. The method of claim 11, wherein the step of determining reservoir rock and fluid characteristic comprises:
    performing X-Ray Diffraction (XRD) and Quantitative Evaluation of Materials by Scanning Electron Microscopy (QEMSCAN) to characterize the mineralogy of the reservoir rock sample.

13. The method of claim 12, wherein the step of determining reservoir rock and fluid characteristic comprises:
    characterizing in-situ wettability utilizing contact angle measurement at reservoir conditions with the reservoir rock sample.

14. The method of claim 13 wherein the step of determining reservoir rock and fluid characteristic comprises:
    determining the effect of pore filling sequence on imbibition, draining and retention of the reservoir rock sample.

15. The method of claim 14, wherein the step of determining reservoir rock and fluid characteristic comprises:
    determining the impact of pore size distribution, microfractures, and pore-fracture connectivity for a fracture-matrix interface for the reservoir rock sample.

16. The method of claim 15, wherein the step of determining reservoir rock and fluid characteristic comprises calculating threshold capillary pressures.

17. The method of claim 16, wherein the step of determining reservoir rock and fluid characteristic comprises:
    calculating propensity of water block due to high capillary pressure, capillary discontinuity, and the impact of wetting state on hydraulic conductance into the matrix during imbibition.

* * * * *